US011229361B2

(12) United States Patent
Coen et al.

(10) Patent No.: US 11,229,361 B2
(45) Date of Patent: Jan. 25, 2022

(54) HEALTH INFORMATION MEASUREMENT SYSTEM

(71) Applicants: Aidan Coen, East Troy, WI (US);
Brietta Coen, East Troy, WI (US);
Avonna Niegelsen, East Troy, WI (US);
Sarah Scanlan, East Troy, WI (US);
Lucy Schrieber, East Troy, WI (US);
Mary Schrieber, East Troy, WI (US);
Hannah Schulgen, East Troy, WI (US);
Olivia Sween, East Troy, WI (US)

(72) Inventors: Aidan Coen, East Troy, WI (US);
Brietta Coen, East Troy, WI (US);
Avonna Niegelsen, East Troy, WI (US);
Sarah Scanlan, East Troy, WI (US);
Lucy Schrieber, East Troy, WI (US);
Mary Schrieber, East Troy, WI (US);
Hannah Schulgen, East Troy, WI (US);
Olivia Sween, East Troy, WI (US)

( * ) Notice: Subject to any disclaimer, the term of this patent is extended or adjusted under 35 U.S.C. 154(b) by 496 days.

(21) Appl. No.: 15/785,701

(22) Filed: Oct. 17, 2017

(65) Prior Publication Data
US 2019/0110684 A1 Apr. 18, 2019

(51) Int. Cl.
*A61B 5/00* (2006.01)
*A61B 5/01* (2006.01)
(Continued)

(52) U.S. Cl.
CPC ............ *A61B 5/0022* (2013.01); *A61B 5/002* (2013.01); *A61B 5/0031* (2013.01); *A61B 5/01* (2013.01);
(Continued)

(58) Field of Classification Search
CPC ........ A61B 2503/40; A61B 2560/0219; A61B 2562/08; A61B 5/002; A61B 5/0022;
(Continued)

(56) References Cited

U.S. PATENT DOCUMENTS 6,113,539 A * 9/2000 Ridenour ............. A61B 5/0002
128/903
6,998,980 B2 2/2006 Ingley, III et al.
(Continued)

OTHER PUBLICATIONS

AlphaTRAK2 Blood Glucose Monitoring Starter Kit, Product ID No. 32107, Available from www.adwdiabetes.com as of 2016.
(Continued)

*Primary Examiner* — Jonathan T Kuo
*Assistant Examiner* — Vynn V Huh
(74) *Attorney, Agent, or Firm* — Foley & Lardner LLP

(57) ABSTRACT

A system includes an implant configured to be inserted subcutaneously into an individual, a transceiver configured to communicate wirelessly with the implant, and a database provided with at least one of the transceiver, a user device, and a remote storage device. The implant includes a sensor module configured to measure data relating to a health of the individual. The transceiver is configured to provide a first signal to the implant that conveys energy to power the implant and a second signal to the transceiver that contains the data. The database is operatively coupled to the transceiver and configured to store the data. The at least one of the transceiver, the user device, and the remote storage device include a processing circuit configured to access the database and provide the data to a user.

6 Claims, 12 Drawing Sheets

(51) Int. Cl.
  A61B 5/0255     (2006.01)
  A61B 5/11       (2006.01)
  A61B 5/145      (2006.01)
  A61B 5/021      (2006.01)
  G16H 40/67      (2018.01)

(52) U.S. Cl.
  CPC .......... *A61B 5/0255* (2013.01); *A61B 5/1118* (2013.01); *A61B 5/14532* (2013.01); *A61B 5/021* (2013.01); *A61B 2503/40* (2013.01); *A61B 2560/0219* (2013.01); *A61B 2562/08* (2013.01)

(58) Field of Classification Search
  CPC ......... A61B 5/0031; A61B 5/01; A61B 5/021; A61B 5/0255; A61B 5/1118; A61B 5/14532
  See application file for complete search history.

(56) References Cited

U.S. PATENT DOCUMENTS

| | | | | |
|---|---|---|---|---|
| 2001/0037056 A1* | 11/2001 | Nunome | ............... | A61B 5/0002 600/300 |
| 2002/0010390 A1* | 1/2002 | Guice | ................... | A61B 5/0031 600/300 |
| 2003/0100040 A1* | 5/2003 | Bonnecaze | ........ | A61B 5/14514 435/14 |
| 2012/0029311 A1* | 2/2012 | Raptis | .................... | G16H 10/60 600/300 |
| 2014/0257115 A1* | 9/2014 | Katra | ....................... | A61B 5/04 600/483 |
| 2014/0275824 A1* | 9/2014 | Couse | .................... | G16H 40/60 600/301 |
| 2015/0157435 A1* | 6/2015 | Chasins | .................. | A61B 5/01 600/301 |
| 2017/0030882 A1* | 2/2017 | Skoda | .................... | G01N 33/15 |
| 2020/0015740 A1* | 1/2020 | Alnofeli | ............... | A61B 5/4845 |

OTHER PUBLICATIONS

Animal Rights, "Top 11 Animal Rights Issues", by Doris Lin dated Aug. 9, 2016.
Applied Animal Behavior Science, "Animal-visitor interactions in the modern zoo—Conflicts and interventions", vol. 120, Issues 1-2, Aug. 2009, pp. 1-8.
AVMA "Microchipping of Animals FAQ", date accessed Sep. 11, 2016, from https://www.avma.org/KB/Resources/FAQs/Pages/Microchipping-of-animals-FAQ.aspx.
AZ State Univeristy, Dept. of Chemical Bio Materials Engineering, "Thermoelectric enzyme sensor for measuring blood glucose", dated Jan. 1, 1990.
Brem, Barbara, "Zoo Walkways: The Path to Connecting with Nature." dated 2012.
Dog Time, "Top 10 Signs of Cancer in Dogs," by Christine McLaughlin, date accessed 2016 from https://dogtime.com/dog-health/canine-cancer/19958-top-10-signs-of-cancer-in-dogs.
Donna Solomon, DVM, "Everything you always wanted to know about your pet's urine," date accessed 2016.
High Tech Pet, "Bluetooth Electronic Fence, Remote Trainer & Bark Control Collar", date accessed Feb. 10, 2017 from http://www.hitecpet.com/x-22-bluetooth-electronicdogfence.html.
Humane Society of Southern WI, "Microchipping," date accessed 2016 from https://www.petsgohome.org/services/microchipping/.
Microchip Technology Inc. "Microchip—Get in Touch with Microchip", date accessed Jan. 2, 2017 from http://www.microchip.com.
Microchip Technology, Inc. "Microchip", date accessed Jan. 2, 2017 from http://www.microchip.com/.
National Center for Health Research, "The benefits of pets for human health", by Dana Casciotti, PhD and Diana Zuckerman, PhD, date accessed Sep. 12, 2016 from http://center4researchorg/healthy-living-prevention/pets-and-health-the-impact-of-compan . .
Pet Education, "Lyme Disease (*Borreliosis*) in Dogs," by Drs. Foster & Smith, date accessed 2016 from http://peteducation.com/article.cfm?c=2 2102&aid=458.
Pet MD, "Pain (Acute, Chronic ana Postoperative) in Dogs," date accessed 2016 from https://www.petmd.com/dog/conditions/neurological/c_multi_pain.
PETA, "Animals Are Not Ours to Eat, Wear, Experiment on, Use for Entertainment or Abuse in any other way," date accessed 2016 from http://www.peta.org/issues/animals-in-entertainment/animals-used-entertainment-factsheets/zoos-pitiful-prisons.
Petfinder, "How do Pet Microchips Work?", date accessed Nov. 5, 2016 from https://www.petfinder.com/dogs/lost-and-found-dogs/how-pet-microchips-work/.
Petfinder, "Pet Microchip FAQs," date accessed 2016 from https://www.petfinder.com/dogs/lost-and-found-dogs/microchip-faqs/.
Petpace, "Petpace Smart-Sensing Collar," date accessed 2016 from https://petpace.com/.
Scientific American, "Rise in Roadkill Requires New Solutions", by Melissa Gaskill dated May 16, 2013.
Sensors, "Wireless applictions, RDID Microchip to Monitor Animals' Body Temperature" dated Apr. 12, 2006 from http://www.sensorsmag.com/networking-communications/wireless-app . . . .
Silicon Labs, "UG250 Thunderboard Sense Users' Guide" dated Sep. 26, 2016.
Stanley Coren, Ph.D.,F.R.S.C., "How many dogs are there in the World?" date accessed Oct. 16, 2016 from https://www.psychologytoday.com/blog/canine-corner/201209/how-many-dogs-are-there . . . .
Submission to forms.whitehouse.gov dated Oct. 17, 2016.
The Humane Society of the United States, "High Tech: Identifying Lost Pets with Microchips," date accessed 2016 from https://www.humanesociety.org/resources/high-tech-identifying-lost-pets-microchips.
The Humane Society, "Pets by the Numbers", date accessed Oct. 16, 2016 from http://www.humanesociety.org/issues/pet_overpopulation/facts/pet_ownership_statistics.
VetScan Canine Rapid Lyme Test Kit, Product ID No. 50485, Available from www.allivet.com as of 2016.
WEBMD, "Fever in Dogs," date accessed 2016 from https://pets.webmd.com/dogs/high-fever-in-dogs.
WEBMD, "Fevers in Cats," date accessed 2016 from https://pets.webmd.com/cats/fevers-in-cats.
Wikipedia, "Microchip implant (animal)", date accessed Sep. 30, 2016 from https://en.wikipedia.org/wiki/microchip_implant_(animal).
Zaa, "Animal Care & Enclosure Standards and Related Polices" dated Dec. 29, 2015.

* cited by examiner

HEALTH INFORMATION MEASUREMENT SYSTEM

BACKGROUND

The present application relates generally to the field of implantable devices. In particular, the present application relates to implantable devices configured to measure information relating to a health of an individual. Individuals, both human and animal, sometimes have difficulty knowing that they are sick or expressing that they are sick to their caretakers. By way of a first example, domestic companion animals, such as dogs or cats, may lack an ability to adequately express the condition of their health to their owners. In such a situation, the owners' only indication of a problem with the animal may be a change in the animal's behavior, which may also be influenced by other factors, potentially leading to an inaccurate diagnosis. By way of another example, certain species of animals are known to hide sickness from others to prevent showing weakness in their social structures. Conventionally, this may prevent a keeper from detecting sickness within a population of animals. By way of yet another example, in certain situations (e.g., during space travel) the health conditions of a human individual are monitored on a regular basis to detect signs of illness and/or another condition. Conventional health measurement techniques (e.g., external thermometers and blood pressure cuffs, etc.) are time consuming and cumbersome, preventing the individual from performing other activities.

SUMMARY

One exemplary embodiment relates to a system including an implant configured to be inserted subcutaneously into an individual, a transceiver configured to communicate wirelessly with the implant, and a database provided with at least one of the transceiver, a user device, and a remote storage device. The implant includes a sensor module configured to measure data relating to a health of the individual. The transceiver is configured to provide a first signal to the implant that conveys energy to power the implant and a second signal to the transceiver that contains the data relating to the health of the individual. The database is operatively coupled to the transceiver and configured to store the data relating to the health of the individual. The at least one of the transceiver, the user device, and the remote storage device include a processing circuit configured to access the database and provide the data relating to the health of the individual to a user.

Another exemplary embodiment relates to a method of monitoring a health of an individual including inserting an implant subcutaneously into the individual, the implant including a sensor module configured to measure data relating to the health of the individual, providing a first signal to the implant that conveys energy to power the implant, receiving a second signal from the implant that contains the data relating to the health of the individual, storing the data in a database, and providing the data to a user.

Yet another exemplary embodiment relates to an implant for an individual including a sensor module, an antenna array including at least one antenna, a controller operatively coupled to the sensor module and the antenna array, and a housing configured to contain the sensor module, the antenna array, and the controller. The sensor module includes a temperature sensor configured to measure a body temperature of the individual, a blood glucose sensor configured to measure a blood glucose level of the individual, a heart rate sensor configured to measure a heart rate of the individual, and a movement sensor configured to measure a movement level of the individual. The antenna array is configured to (a) receive a first signal from a transceiver located outside of the individual and (b) emit a second signal to the transceiver. The controller includes a processing circuit configured to control communication from the implant to the transceiver. The implant is configured to be inserted subcutaneously into the individual and use energy associated with the first signal to power the controller and the sensor module. The second signal includes the body temperature of the individual, the blood glucose level of the individual, the heart rate of the individual, and the movement level of the individual.

The invention is capable of other embodiments and of being carried out in various ways. Alternative exemplary embodiments relate to other features and combinations of features as may be recited herein.

BRIEF DESCRIPTION OF THE DRAWINGS

The disclosure will become more fully understood from the following detailed description, taken in conjunction with the accompanying figures, wherein like reference numerals refer to like elements, in which.

DETAILED DESCRIPTION

Before turning to the figures, which illustrate the exemplary embodiments in detail, it should be understood that the present application is not limited to the details or methodology set forth in the description or illustrated in the figures. It should also be understood that the terminology is for the purpose of description only and should not be regarded as limiting.

According to an exemplary embodiment, a health information measurement system includes an implant configured to be inserted subcutaneously (i.e., below the skin) into an individual (e.g., an animal, a human, etc.). After insertion, the implant is configured to routinely measure a number of different types of health measurement data that relate to the health of the individual. The implant may be configured to measure body temperature, heart rate, movement, blood sugar, blood pressure, and/or other information. The implant is configured to receive an interrogation signal wirelessly from a transceiver, the interrogation signal providing power to the implant. In response to receiving the interrogation signal, the implant is configured to emit a response signal back to the transceiver, the response signal containing the health measurement data. The system is configured to store the data in a database (e.g., on the transceiver, in a remote storage system, on a mobile device, etc.). The health measurement data can be viewed by a user (e.g., on a display) using a user device or using the transceiver. The system is further configured to analyze the health measurement data to determine if there are any abnormalities in the data or other signs of illness. If illness is detected, the system is configured to notify the user.

Figure 1:
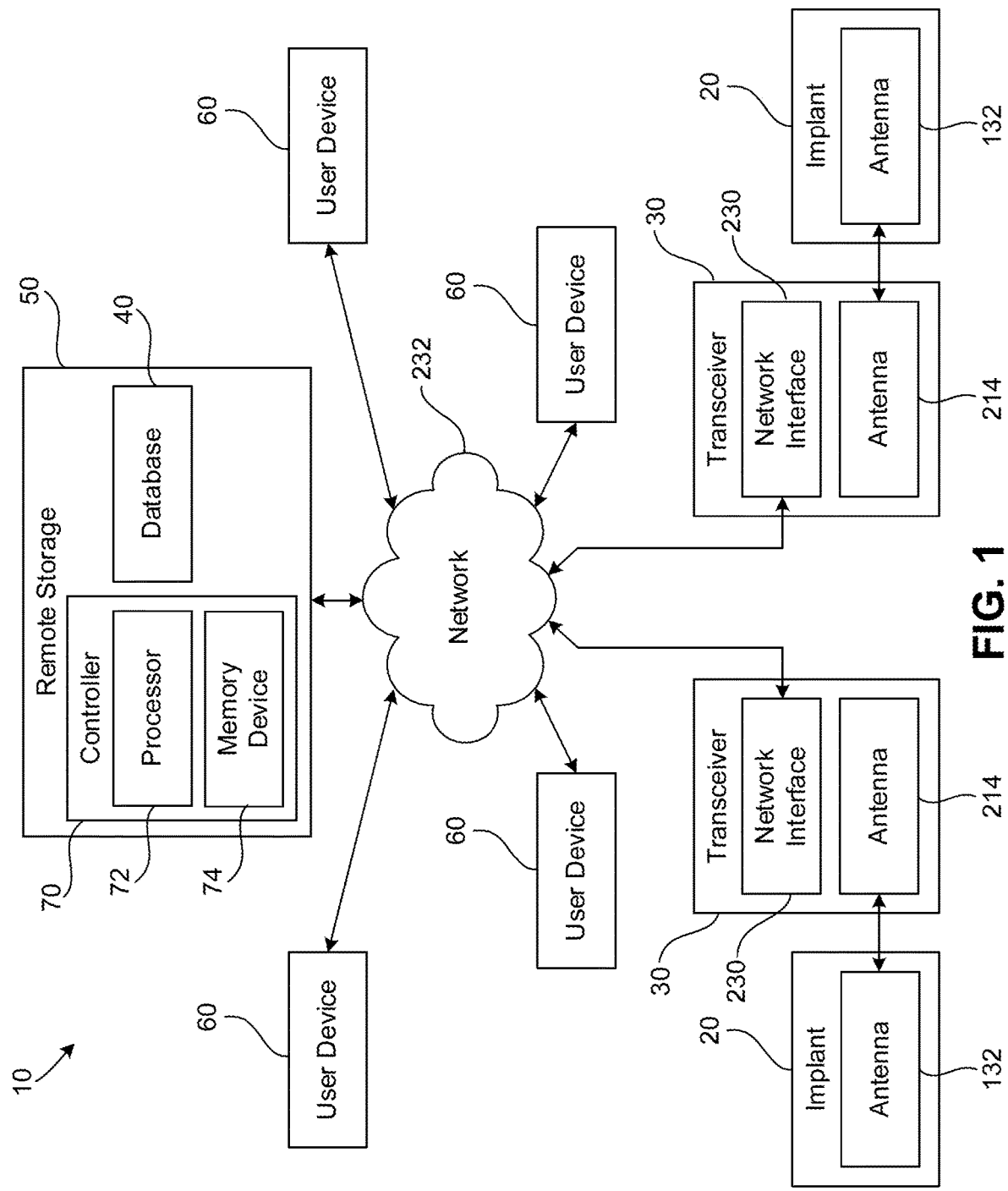
FIG. 1 is a block diagram of a health information measurement system, according to an exemplary embodiment.

Referring to FIG. 1, a health information measurement system or health monitoring system, shown as system 10, includes a health information measurement device or implant, shown as implant 20, configured to be implanted subcutaneously into an individual (i.e., beneath the skin of the individual). The implant 20 is configured to measure information (e.g., quantities, statuses, etc.), referred to herein as health measurement data, directly or indirectly relating to the health of the individual. An interrogation device, shown as transceiver 30, is configured to communicate wirelessly with the implant 20 to provide power to the implant 20 and receive the health measurement data. The health measurement data may be viewed directly on the transceiver 30, or stored in a database 40. In some embodiments, the database 40 is located in an enterprise computing system or cloud-based storage system, shown as remote storage device or remote storage 50. Alternatively, the database 40 may be stored in a memory device in the transceiver 30 or a user device 60. The user device 60 displays the data (e.g., in a graphical user interface (GUI)) to facilitate review of the health measurement data by a user.

The system 10 further includes a controller 70 configured to control the operation of the system 10. The controller 70 includes a processing circuit or processing device, shown as processor 72, and a memory or memory device, shown as memory device 74. The controller 70 is configured to access the database 40 (e.g., to store data, to review or analyze data, to transfer data to another component, etc.). In some embodiments, the controller 70 reviews or analyzes the health measurement data to and determines whether any of the health measurement data is abnormal or indicates a potential health risk to the individual. The controller 70 provides (e.g., through a display on the transceiver 30 or the user device 60) a user with the data directly and/or with the results of the analysis.

As used herein, an "individual" refers to any type of human or animal. The individual may be a domestic companion animal (e.g., dogs, cats, etc.), wildlife (e.g., deer, birds, fish, etc.), a zoo animal, or a farm animal (e.g., cattle, swine, chickens, etc.). The individual may be a member of any of the various animal classes (e.g., mammals, reptiles, birds, fish, amphibians, etc.). The implant 20 may be configured specifically based on the intended type of individual. By way of example, the size of the implant 20 and the types of sensors included in the implant 20 may vary depending upon the type of individual. As used herein, a "user" manages the health of one or more individuals. The user may be a pet owner, a veterinarian, a zookeeper, a farmer, a doctor, or the individual themselves.

Figure 2B:
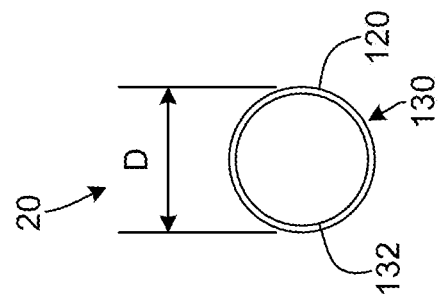
FIG. 2B is a side view of the implant of FIG. 2A.
Figure 2A:
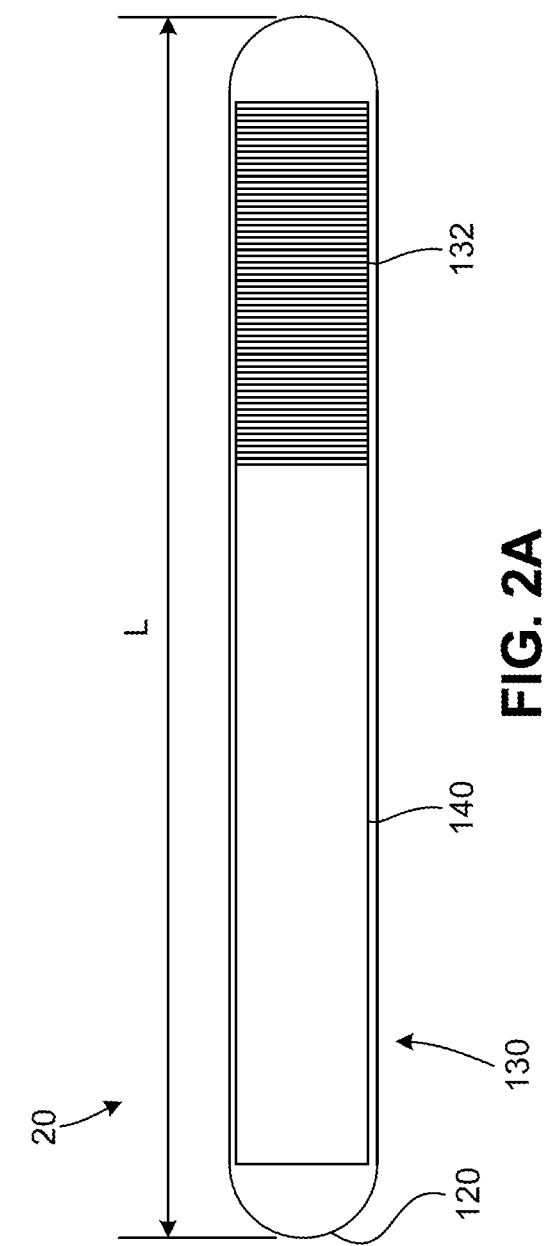
FIG. 2A is a top view of an implant of the health information measurement system of FIG. 1.

Referring to FIGS. 2A and 2B, the implant 20 is shown. The implant 20 is configured to be inserted subcutaneously into an individual. The implant 20 includes a shell, coating, or housing 120 that is configured to contain and protect a transponder 130. The transponder 130 is configured to receive an interrogation signal from a transceiver 30 and emit a response signal back to the transceiver 30. The interrogation signal is converted to electrical energy to power the implant 20 and may contain information (e.g., commands). The response signal contains health measurement data measured by one or more sensors included in the transponder 130.

Referring to FIG. 1, the housing 120 is shown as having a primarily cylindrical shape with rounded ends. The cylindrical portion of the housing 120 has a diameter D, and the housing 120 has an overall length L. When inserting the implant 20 into an individual, the implant 20 may be injected under the skin using a syringe and a needle. In one such example, the needle of the syringe passes through the skin, and the syringe is depressed, forcing the implant through the needle and under the skin. Accordingly, the diameter D of the cylindrical portion may be a standard size to facilitate movement of the implant 20 through a common needle. The diameter D may be slightly smaller than the inner diameter of the needle. The overall length L may vary depending upon the functionality of the implant 20 and the components included in the implant 20.

The housing 120 is formed from a biocompatible material. As used herein, a material is considered to be biocompatible if it does not cause a negative local or systemic reaction in the individual. The material used to form the housing 120 is nontoxic. The material may be a polymer, glass, or another material. In some embodiments, the material is configured to prevent migration of the implant 20 throughout the body of the individual after insertion. The housing 120 contains the transponder 130 and prevents corrosion or other wear of the transponder 130 due to contact with the body of the individual. In some embodiments, an extension, such as a probe or electrode from one of the sensors included in the transponder 130, extends through the housing 120 to contact the body.

In some embodiments, the housing 120 and the transponder 130 are made using materials that will dissolve, degrade (e.g., biodegrade), or otherwise break down in the body of the individual after an operational time period has passed. Such an embodiment is useful in a situation where the system 10 will only be used for a set period of time. The use of dissolvable materials facilitates noninvasive removal of the implant 20 (e.g., without surgery). In some embodiments, the housing 120 and the transponder 130 have different operational time periods once exposed to the body. By way of example, the operational time period of the housing 120 may be significantly longer than that of the operational time period of the transponder 130. In such an example, the operational time period of the implant 20 is approximately equal to the operational time period of the housing 120.

Figure 3:
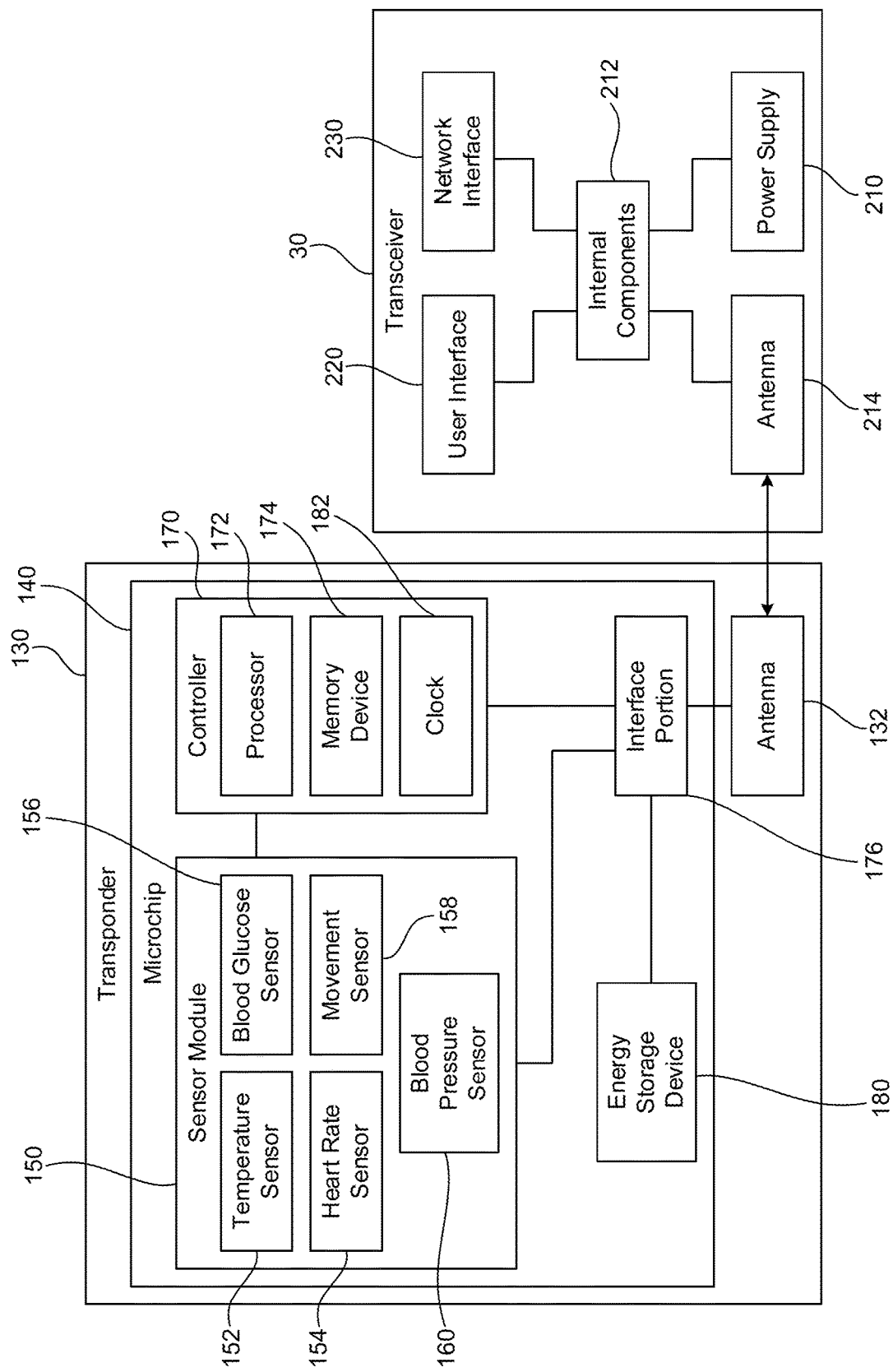
FIG. 3 is a block diagram of the implant of FIG. 2A and a transceiver of the health information management system of FIG. 1.

Referring to FIG. 3, the transponder 130 includes an antenna array, shown as antenna 132, operatively coupled to a circuit, shown as microchip 140. The antenna 132 is configured to receive the interrogation signal and provide it to the microchip 140. The antenna 132 is further configured to emit the response signal. The antenna 132 may include one or more individual antennae. Although the antenna 132 is shown as a single antenna that both emits and receives signals, it should be understood that the transponder 130 may include separate emission and reception antennae. The antenna 132 is arranged in a coil shape having a number of windings. In some embodiments, the microchip 140 is a single integrated circuit. In other embodiments, the microchip 140 may be multiple integrated circuits connected together. The microchip 140 includes a sensor module 150. The sensor module 150 includes one or more sensors configured to measure medical information (i.e., health measurement data) of the individual. The sensor module 150 may include one or more of a temperature sensor 152 configured to measure body temperature, a heart rate sensor 154 configured to measure a heart rate, a blood glucose sensor 156 configured to measure a blood glucose level, a movement sensor 158 configured to measure a movement level, and a blood pressure sensor 160 configured to measure blood pressure. In other embodiments, the sensor module 150 additionally or alternatively includes other types of sensors.

In some embodiments, the sensor module 150 includes a temperature sensor 152. The temperature sensor 152 is configured to measure a temperature of the surroundings of the implant 20 (e.g., a body temperature). The temperature sensor may be any type of sensor capable of sensing a body temperature. By way of example, the temperature sensor may be a resistance temperature detector (RTD) or a thermistor. In other embodiments, the temperature sensor 152 may be another type of sensor capable of measuring a temperature. The controller 70 may be configured to determine a healthy range for the body temperature of the individual. In some embodiments, the controller 70 determines or varies the healthy range based on the species of the individual. The controller 70 may determine that the individual is experiencing an illness if the body temperature falls outside of the determined healthy range.

In some embodiments, the sensor module includes a heart rate sensor 154. The heart rate sensor 154 is configured to measure the frequency of heart rhythms (i.e., a heart rate) of the individual in which the implant 20 is inserted. The heart rate sensor 154 may be an electrocardiography (ECG) sensor that measures electrical signals from expansion and contraction of the heart, a photoplethysmography (PPG) sensor that utilizes light to visually monitor the rate of blood flow, or another type of heart rate sensor. The heart rate sensor 154 may include an electrode that extends through the housing 120, or may sense the heart rate through the housing 120. The controller 70 may be configured to determine a healthy range for a heart rate of the individual. The controller 70 may determine or vary the healthy range based on a number of factors, including the age, the species, and the current activity level of the individual. The controller 70 may cooperate with a movement sensor 158 to determine a healthy range for heart rate of the individual. By way of example, the controller 70 may set the healthy range higher if the movement sensor 158 indicates that the individual has recently been physically active.

In some embodiments, the sensor module 150 includes a blood glucose sensor 156. The blood glucose sensor 156 is configured to measure a blood sugar level or blood glucose level of the individual. The blood glucose level is monitored closely in individuals with certain diseases, such as diabetes. Accordingly, the blood glucose sensor 156 may be omitted in certain embodiments where the implant 20 is configured for use with an individual without such a disease. The blood glucose sensor 156 may measure blood glucose levels electrochemically or using another known method. Accordingly, the blood glucose sensor 156 may include a probe that extends through the housing 120 to contact fluids surrounding the implant 20. The controller 70 may determine and/or vary a healthy range for the blood glucose level of the individual based on a number of factors, including the species of the individual.

In some embodiments, the sensor module 150 includes the movement sensor 158. The movement sensor 158 may be configured to detect and/or measure movement of the movement sensor 158. By way of example, a movement sensor 158 may be configured to measure a speed, acceleration, and/or direction of travel of the movement sensor 158. The movement sensor 158 may be an accelerometer, a gyroscopic sensor, or another type of sensor capable of detecting and/or measuring movement. Due to the location of the implant 20 within the individual, movement of the movement sensor 158 corresponds to a movement level of the individual. The controller 70 may use the determined movement level of the individual when determining the state of health of the individual directly, or use it indirectly in combination with information from another sensor, such as the heart rate sensor 154. The controller 70 may determine and/or vary a healthy range for the movement level of the individual based on a number of factors, including a species of the individual, an age of the individual, the time of day (e.g., as measured using the clock 182), an outside temperature (e.g., retrieved from an internet database), or other factors. The healthy range for the movement level may be based on a total distance traveled in a certain period of time, an average movement speed, or another metric relating to the movement of the individual. By way of example, the controller 70 may determine that an individual is experiencing an illness if the average speed of the individual is lower than a threshold speed for greater than a threshold period of time.

In some embodiments, the sensor module 150 includes a blood pressure sensor 160. The blood pressure sensor 160 is configured to measure a blood pressure of the individual. The blood pressure sensor 160 may be a pressure sensor, a sensor configured to measure electrical signals from the heart, or another type of sensor. Accordingly, the blood pressure sensor 160 may include electrodes or probes that extend through the housing 120. The controller 70 may be configured to determine a healthy range for the blood pressure of the individual (e.g., based in part on the species of the individual). The controller 70 may determine that the individual is experiencing an illness if the blood pressure falls outside of the healthy range.

Referring to FIG. 3, the microchip 140 further includes a controller 170 operatively coupled to the sensor module 150 and the antenna 132. In one embodiment, the controller 170 is configured to control the operation of the sensor module 150 and the transmission and reception of signals through the antenna 132. The controller 170 includes a processing circuit or processor 172 and a memory or memory device 174. The processor 172 is configured to receive and process information from the other components. In some embodiments, the processor 172 is configured to convert an output of the sensor module 150 (e.g., a voltage, a current, a resistance) into health measurement data (e.g., a body temperature, a blood pressure, etc.). The processor 172 may be configured to issue commands to other components. By way of example, the processor 172 may initiate the measurement of health measurement data by the sensor module 150. The processor 172 can be implemented as a general purpose processor, an application specific integrated circuit (ASIC), one or more field programmable gate arrays (FPGAs), a group of processing components, or other suitable electronic processing components.

The memory device 174 (e.g., memory, memory unit, storage device, etc.) is one or more devices (e.g., RAM, ROM, flash memory, hard disk storage, etc.) for storing data and/or computer code for completing or facilitating the various processes, layers and modules described in the present application. The memory device 174 may be or include volatile memory or non-volatile memory. The memory device 174 may include database components, object code components, script components, or any other type of information structure for supporting the various activities and information structures described in the present application. The processor 172 and the memory device 174 are configured to cooperate to control the measurement and storage of health measurement data using the sensor module 150 (e.g., multiple sets of health measurement data measured at different points in time). By way of example, the processor 172 may transfer the health measurement data measured by the sensor module 150 to the memory device 174, and the memory device 174 may store the health measurement data.

Referring to FIG. 3, the microchip 140 further includes an interface portion 176. The interface portion 176 is configured to connect the microchip 140 to the antenna 132. The interface portion 176 receives the interrogation signal through the antenna 132 and distributes electrical power and data to the other components of the microchip 140. To power the transponder 130, the antenna 132 converts the interrogation signal into electrical energy through induction, providing an alternating current (AC) power supply to the interface portion 176. The ratio between the number of windings in the antenna 132 of the implant 20 and the number of windings in the antenna 214 of the transceiver 30 may be adjusted to adjust the voltage of the electrical energy supplied to the interface portion 176. The interface portion 176 may include various circuit components to facilitate the distribution of electrical power to the other components of the microchip 140. The interface portion 176 may include a rectifier circuit to convert the AC power supply from the antenna 132 into a direct current (DC) power supply. The interface portion 176 may include one or more voltage regulators to regulate the voltage of the electrical power supplied to each component and/or one or more current limiters to prevent damage to system components due to an application of excessive current. The interface portion 176 may provide multiple similarly-configured power supplies (e.g., supplying similar voltages and currents, all AC or all DC) or multiple differently-configured power supplies (e.g., supplying different voltages or currents, some AC and some DC, etc.), depending on the requirements of each specific component. In some embodiments where the interrogation signal contains data (e.g., a command to begin sending health measurement data, a command to erase the health measurement data stored in the memory device 174, etc.), the interface portion 176 may be configured to provide the data to the appropriate component (e.g., to the processor 172, to the memory device 174, etc.).

The microchip 140 is configured to cooperate with the antenna 132 to emit the response signal back to the transceiver 30. The response signal contains the health measurement data from the sensor module 150. The processor 172 may be configured to retrieve the health measurement data from the memory device 174 and provide it to the interface portion 176. The interface portion 176 may include components to facilitate cooperation with the antenna 132 in order to output the response signal. The processor 172 may be configured to command the interface portion 176 to emit the response signal.

In some embodiments, such as the embodiment shown in FIG. 3, the microchip 140 further includes an energy storage device 180. The energy storage device 180 facilitates operation of the transponder 130 and/or the sensor module 150 (e.g., measurement and storage of health measurement data, etc.) when the transponder is not receiving the interrogation signal. The energy storage device 180 may be a battery, a capacitor, or another type of device capable of repeatedly storing energy (e.g., as chemical energy) and discharging energy (e.g., electrical energy). The energy storage device 180 is connected to the interface portion 176. In practice, energy provided to the interface portion 176 when receiving the interrogation signal is stored in the energy storage device 180. Energy from the energy storage device 180 is provided to the other components of the transponder 130 (e.g., the sensor module 150, the processor 172, the memory device 174, etc.), directly or through the interface portion 176. The energy storage device 180 may be used to power the transponder 130 when reception of the interrogation signal is intermittent. By way of example, the energy storage device 180 may be added in an application where the individual is unlikely to stay within range of the transceiver 30 for a sufficient period of time to complete a reading of the sensors and a transfer of the health measurement data. In such an example, the energy storage device 180 provides continuous power regardless of an intermittent reception of the interrogation signal. In another embodiment, the energy storage device 180 is configured to power the transponder 130 for an extended period of time (e.g., minutes, hours, days, weeks, months, etc.) sufficient to facilitate measurement of health measurement data at multiple points in time prior to reconnecting with the transceiver 30.

In some embodiments, the controller 170 further includes a timekeeper or timekeeping device, shown as clock 182, that is configured to measure and provide date and time data relating to the passage of time (e.g., the time of day, the date, a passage of time from a starting point, etc.). The clock 182 facilitates associating a date and/or time with each set of health measurement data (e.g., each set of data points from the temperature sensor 152, the heart rate sensor 154, the blood glucose sensor 156, the movement sensor 158, and/or the blood pressure sensor 160 taken at a single point in time). Accordingly, the date and time data may be contained in the response signal, the database 40 may be configured to contain the date and time data in addition to the health measurement data, and the controller 70 may be configured to associate each set of health measurement data with an associated date and an associated time at which it was measured. Alternatively, the controller 170 may associate each set of health measurement data with the associated date and the associated time prior to emitting the response signal. The clock 182 may continuously consume energy from the energy storage device 180 when measuring the passage of time. In some embodiments, the controller 70 varies the healthy ranges of the health measurement data based on the date and time data provided by the clock 182. By way of example, the controller 70 may set a healthy range of a movement level of an individual to be lower at night when the individual is likely to be sleeping.

In other embodiments, the energy storage device 180 is omitted, and the transponder 130 operates when receiving energy from an outside source (e.g., through the interrogation signal). In some such embodiments, the transponder 130 is configured to begin measuring the medical information (e.g., using the sensor module 150) upon receiving the interrogation signal and emit the response signal immediately after completing the measurements. Upon experiencing a loss of power (e.g., due to an interruption in the reception of the interrogation signal) prior to completion of the measurements, the transponder 130 may be configured to restart the measurement process. Accordingly, embodiments that omit the energy storage device 180 are useful where an interruption in the reception of the interrogation signal is unlikely, as omission of the energy storage device 180 facilitates a reduction in volume of the implant 20.

In some embodiments, the controller 170 is additionally configured to store a unique identifier (e.g., an identification number) or other information relating to the individual corresponding with the implant 20 (e.g., in the memory device 174). The unique identifier may be predefined (e.g., during manufacturing of the implant 20) or may be modified by the user (e.g., by sending a specific command using the transceiver 30). The unique identifier may be associated with the individual corresponding to the implant 20, and may be used to identify the individual. By way of example, a dog may be implanted with the implant 20, and the unique identifier associated with the implant 20 may be stored in a database accessible by a number of entities, such as animal shelters or veterinary clinics, along with contact information for the dog's owners. If the dog were to become separated from its owners, the animal shelter could use the unique identifier to identify the contact information of the owners. In some embodiments, the implant 20 is configured to provide a unique identifier readable by conventional identification microchip scanners. In other instances, the contact information could be stored in the memory device 174 directly. By way of another example, the unique identifier may be used when one user manages a large number of individuals (e.g., a herd of cattle, etc.), each associated with an implant 20. When retrieving health information from one of a large number of individuals, the controller 70 may use the unique identifier to automatically associate the health measurement data with a specific individual, preventing the user from having to manually associate health measurement data with each individual.

Referring to FIG. 3, a block diagram of the transceiver 30 is shown according to an exemplary embodiment. The transceiver 30 includes a power supply 210, electronic components, shown as internal components 212, and an antenna array, shown as antenna 214. The transceiver 30 receives electrical power through the power supply 210 to power the various components of the transceiver 30. The internal components 212 are configured to control the antenna 214 to send the interrogation signal and receive the response signal. In some embodiments, the transceiver 30 further includes a user interface 220 and/or a network interface 230. The user interface 220 facilitates the user providing commands to and/or receiving information from the transceiver 30. The network interface 230 facilitates a data connection between the transceiver 30 and another device.

Figure 5:
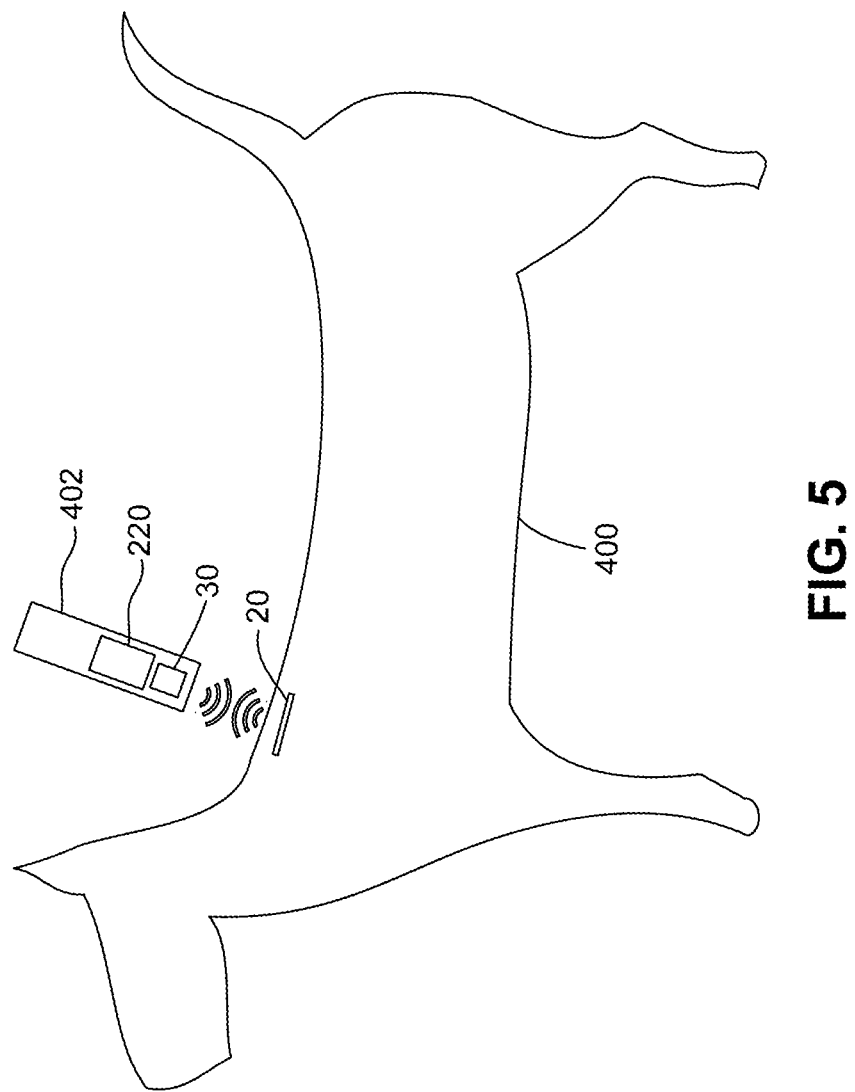
FIG. 5 is a side view showing an arrangement of the implant of FIG. 2A and the transceiver of FIG. 3 configured to monitor a health of a dog, according to an exemplary embodiment.
Figure 6:
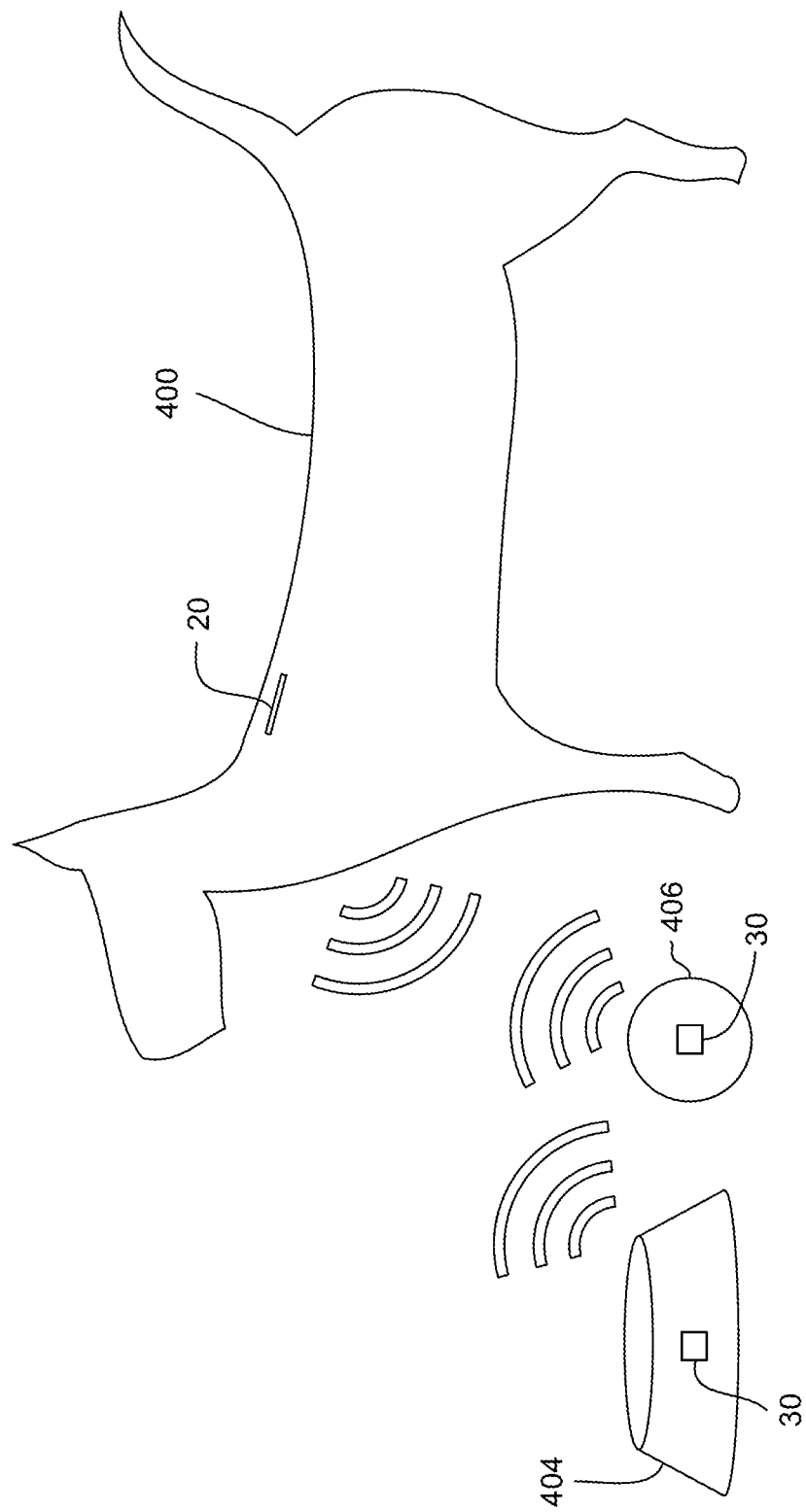
FIG. 6 is a side view showing an arrangement of the implant of FIG. 2A and the transceiver of FIG. 3 configured to monitor a health of a dog, according to an exemplary embodiment.
Figure 7:
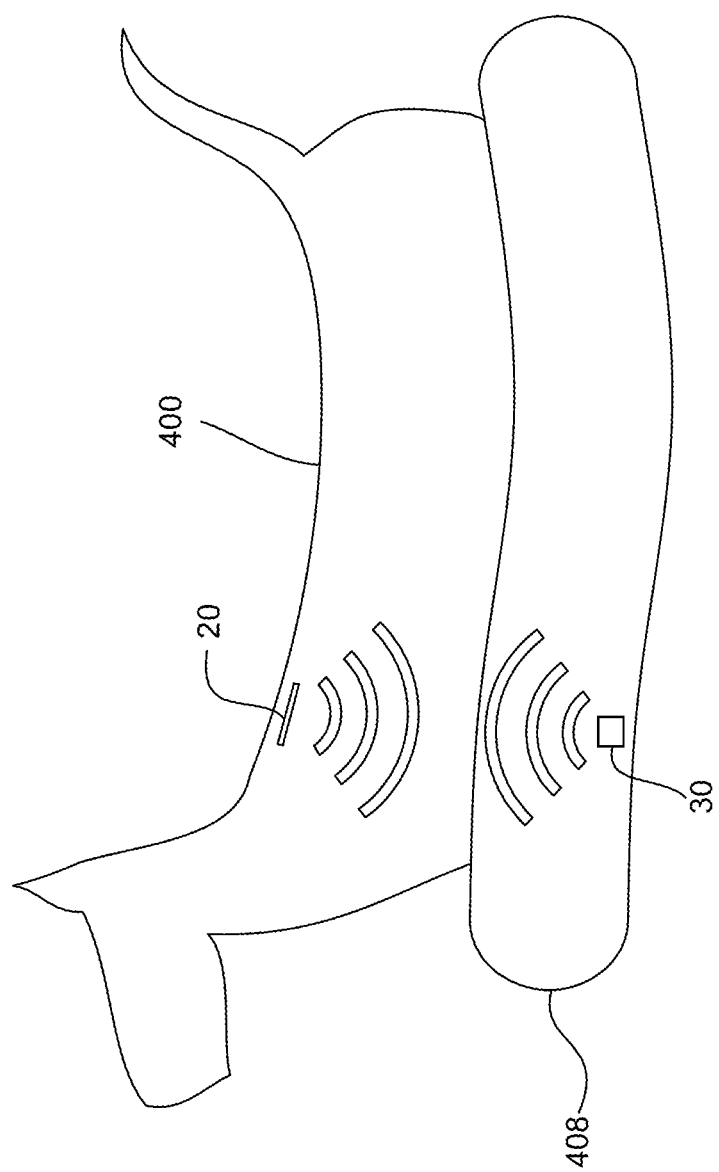
FIG. 7 is a side view showing an arrangement of the implant of FIG. 2A and the transceiver of FIG. 3 configured to monitor a health of a dog, according to an exemplary embodiment.
Figure 8:
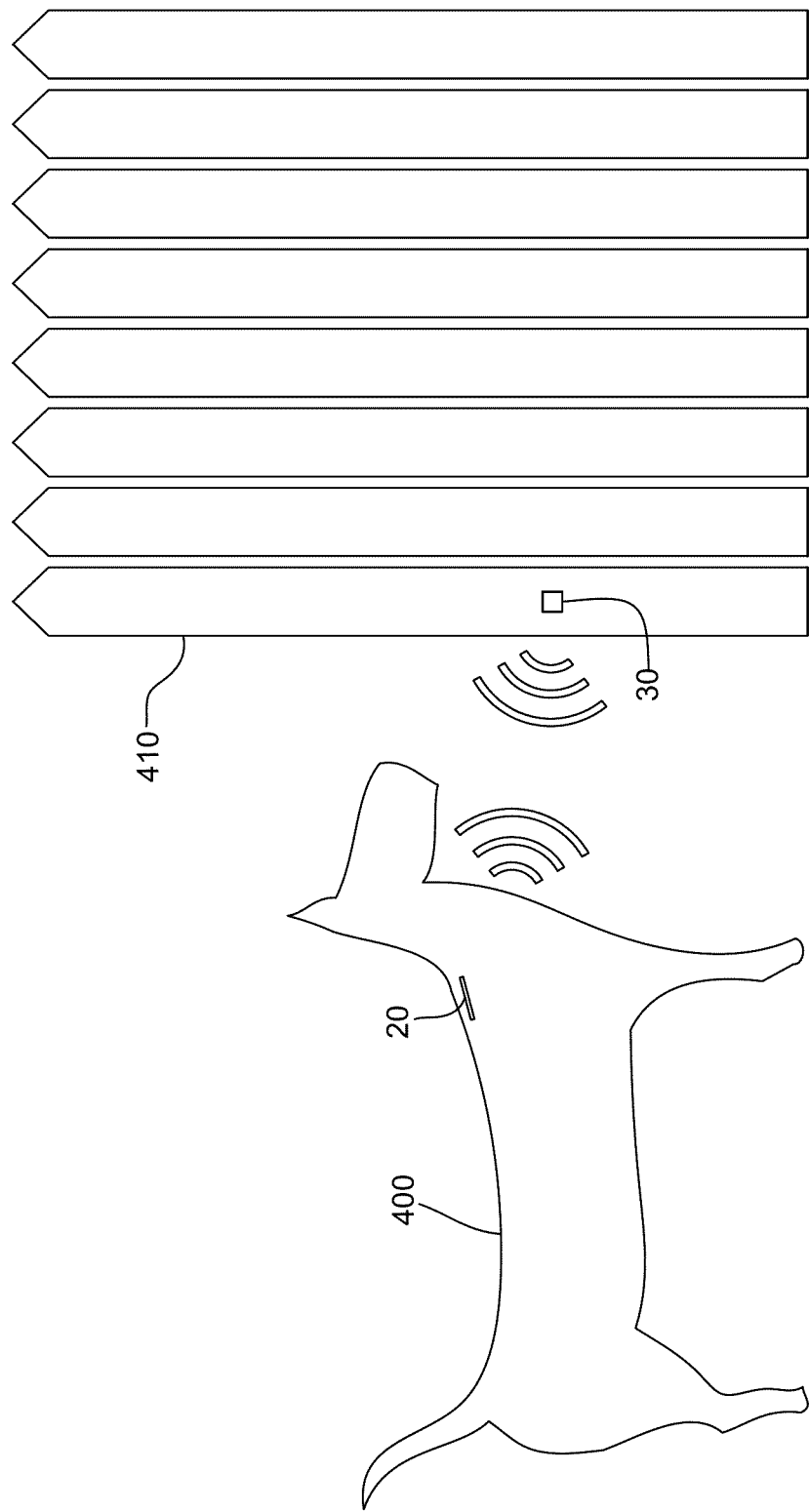
FIG. 8 is a side view showing an arrangement of the implant of FIG. 2A and the transceiver of FIG. 3 configured to monitor a health of a dog, according to an exemplary embodiment.
Figure 9:
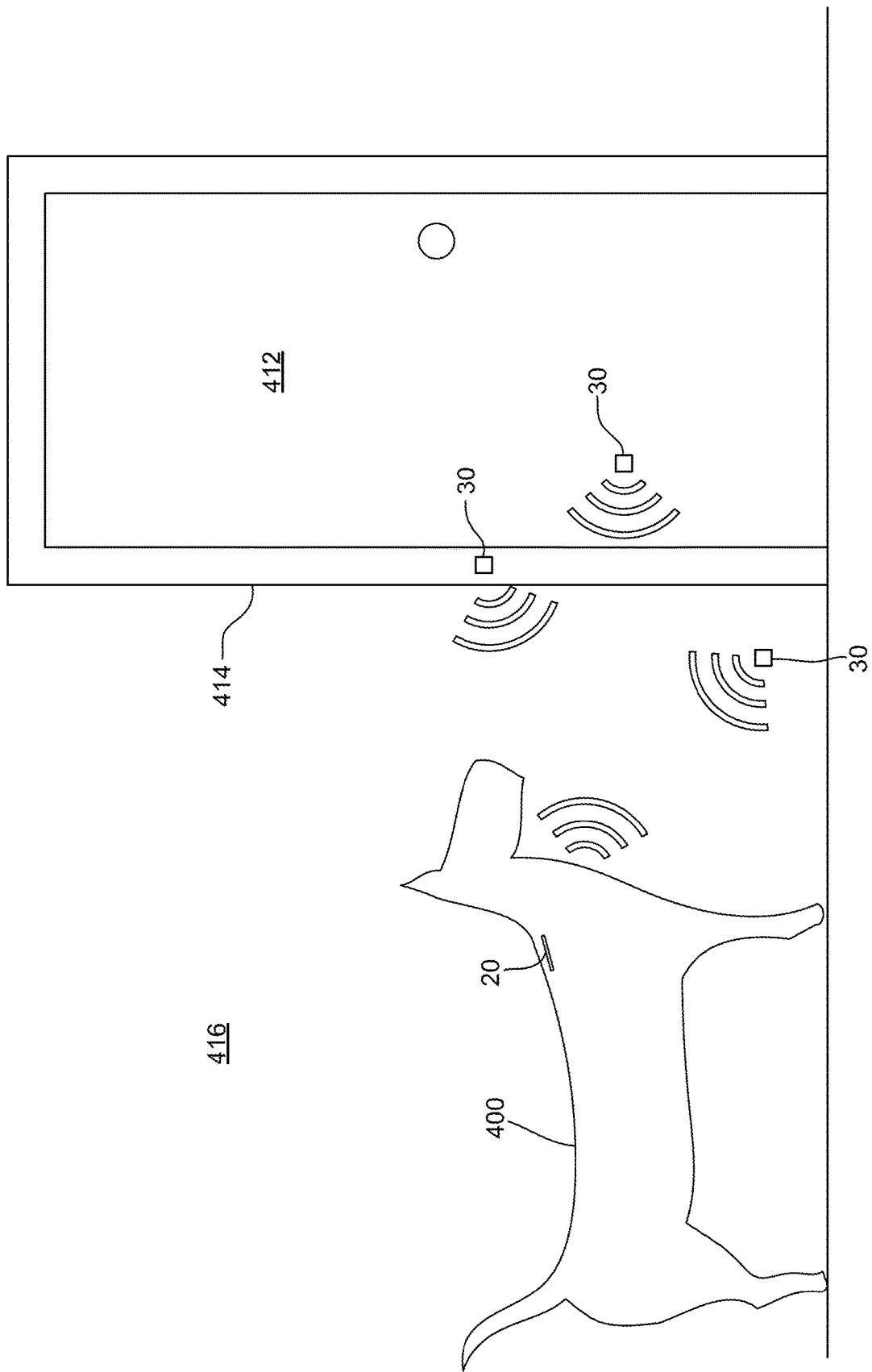
FIG. 9 is a side view showing an arrangement of the implant of FIG. 2A and the transceiver of FIG. 3 configured to monitor a health of a dog, according to an exemplary embodiment.
Figure 10:
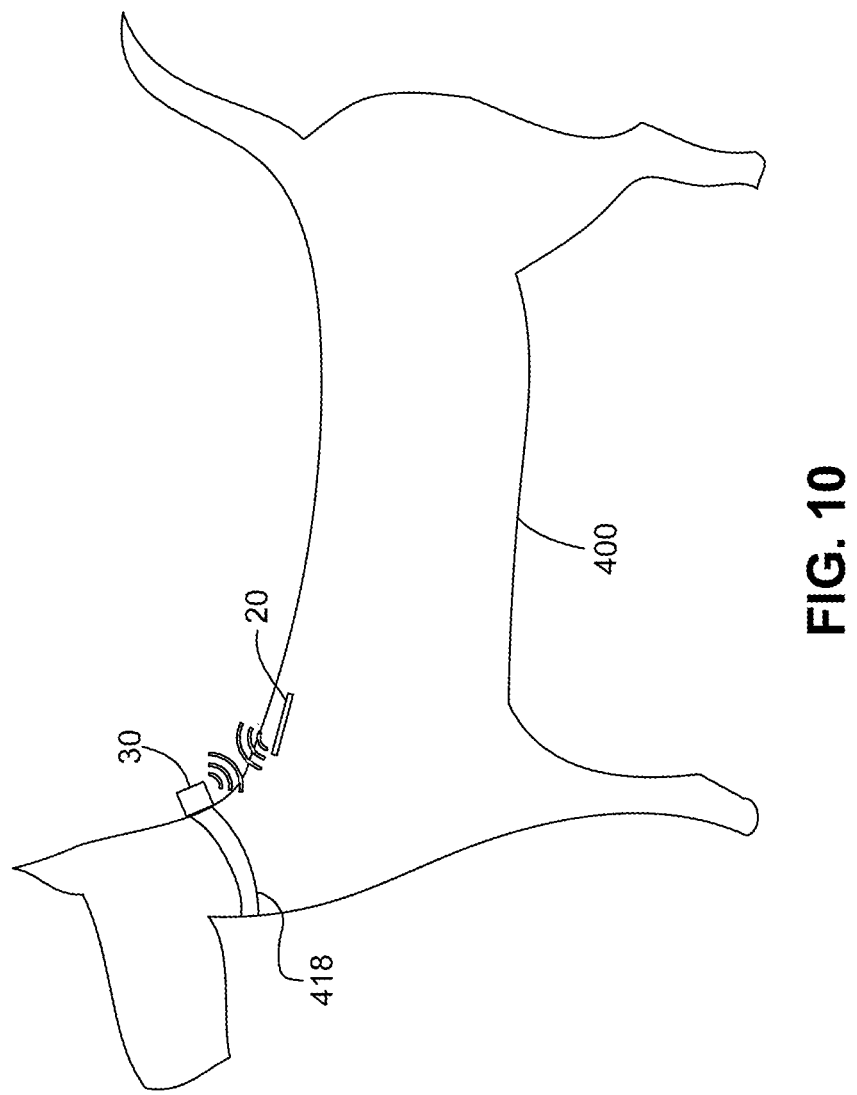
FIG. 10 is a side view showing an arrangement of the implant of FIG. 2A and the transceiver of FIG. 3 configured to monitor a health of a dog, according to an exemplary embodiment.

The transceiver 30 may be configured in a variety of ways depending upon the application of the system 10. In some embodiments, the transceiver 30 is incorporated into a handheld unit that is operated by the user to collect data. By way of example, the user may hold the transceiver 30 up to the individual in the area proximate the implant 20 and interact with the user interface 220 to transmit the interrogation signal (e.g., as shown in FIG. 5). By way of another example, the transceiver 30 may be incorporated into (e.g., coupled to, contained within, etc.) a piece of furniture (e.g., a bed, a chair, a food bowl, etc.) or a portion of a building (e.g., a door frame, a door, a wall, a floor, a counter, etc.) near which the individual passes frequently or stays for extended periods of time (e.g., as shown in FIGS. 6-9, 11, and 12. By way of another example, the transceiver 30 may be configured to be wearable by the individual (e.g., as part of a belt, as part of a collar, etc., as shown in FIGS. 10 and 12). Transceivers 30 that are configured to be wearable or incorporated into a piece of furniture or a part of building facilitate a connection between the implant 20 and the transceiver 30 automatically (i.e., without an action by the user), as the individual is regularly within a close range of such transceivers 30. In some embodiments, the system 10 includes multiple transceivers 30 configured similarly or multiple transceivers 30 configured in a variety of ways (e.g., one handheld transceiver and one wearable transceiver, etc.).

The power supply 210 supplies electrical power to the transceiver 30. The power supply 210 may be a DC power supply or an AC power supply. By way of example, the power supply 210 may be a household power outlet configured to supply AC electrical power to the transceiver 30 through a power cord. By way of another example, the power supply may be an AC power source (e.g., a household power outlet) including a rectifier or other device configured to convert the AC electrical power to DC electrical power. The power supply 210 may include an energy storage device (e.g., a battery, a capacitor, etc.) onboard the transceiver 30. In some such embodiments, the energy storage device is rechargeable from another power source (e.g., a household power outlet) or replaceable.

The internal components 212 and the antenna 214 are configured to cooperate to send the interrogation signal and receive the response signal. In some embodiments, the antenna 214 is a singular antenna capable of sending and receiving signals. In other embodiments, the antenna 214 includes individual antennae for sending and receiving signals. The antenna 214 may be configured into a coil shape having a number of windings to facilitate power transfer to the implant 20 through the interrogation signal. The internal components 212 include a number of electronic components necessary to facilitate operation of the transceiver 30. The internal components 212 facilitate power and data transmission between the various components of the transceiver 30. The internal components 212 may include processing circuits (e.g., the controller 70), memories, rectifiers, voltage regulators, current limiters, and/or other components.

The user interface 220 facilitates interaction between the user and the transceiver 30. The user interface 220 facilitates a user issuing commands to the transceiver 30 and/or provides the user with information. The user interface 220 may include displays, lights, buttons, switches, speakers, touchscreens, or other devices to facilitate user interaction. The user may utilize the user interface 220 to issue commands to begin emitting an interrogation signal, to change the unique identifier of a particular implant 20, to erase the data on the memory device 174, or other commands. The user interface 220 may display a status of the transceiver 30 (e.g., an indication of the connection of the transceiver 30 to the implant 20, the remote storage 50, or the user device 60, a charge level of the power supply 210, etc.) or information related to an implant 20 with which the transceiver 30 is communicating (e.g., what types of sensors are included in the implant 20, current heath measurement data, a charge level of the energy storage device 180, etc.). According to one embodiment, the user interface 220 displays the health measurement data that is currently being transmitted from an implant 20, and the health measurement data is stored in a database 40 on the transceiver 30. In such an embodiment, the remote storage 50 and the user device 60 may be omitted.

The network interface 230 facilitates communication between the transceiver 30, remote storage 50, and/or the user device 60. The network interface 230 may include the hardware and logic to communicate over multiple channels of data communication. The network interface 230 may communicate over wired or wireless communication. For example, the network interface 230 may include a universal serial bus (USB) interface, an Ethernet interface, a Wi-Fi interface, a Bluetooth beacon, a Bluetooth transceiver, a cellular modem, a near field-communication (NFC) transceiver, or another known type of data communication interface.

Referring to FIG. 1, the system 10 includes a network 232 that facilitates communication between the transceiver 30 and other transceivers 30, the remote storage 50, and/or the user devices 60. The transceiver 30 connects to the network through the network interface 230. In some embodiments, the network 232 includes the internet. In other embodiments, the network 232 includes a local area network or a wide area network. The network may be wired, wireless, or a combination thereof. The network 232 may communicate over USB, Ethernet, Wi-Fi, Bluetooth, a cellular connection, NFC, or another known type of data communication.

In some embodiments, the health measurement data from the implant 20 is provided to the database 40. The database 40 is configured to hold, store, categorize, and otherwise serve as a repository for the health measurement data measured by the implant 20. The database 40 may be located in a memory or memory device on the transceiver 30, on the remote storage 50, or on the user device 60. The controller 70 may cooperate with the database 40 to organize the health measurement data based on the date and/or the time the data was measured by the implant 20, the date and/or the time the data was retrieved by the transceiver 30, the date and/or the time the data was added to the database 40, the unique identifier associated with a particular implant 20, the individual corresponding to the data, and/or other factors. The database 40 may store additional information associated with an individual, such as the unique identifier with which they are associated, their name, their gender, their age, known medical information of the individual, and their species. Additionally, in embodiments with multiple users, the controller 70 and the database 40 may cooperate to associate each individual with a particular user. By way of example, if a database 40 were shared amongst multiple veterinary clinics, each individual (e.g., a dog) may be associated with the particular veterinary clinic that provided the individual with their implant 20.

In some embodiments, the database 40 is located on the remote storage 50. The remote storage 50 may be an enterprise computing system, a cloud-based storage system, or another known type of storage system. The remote storage 50 is connected to the network 232 and accordingly is connected to the transceiver 30.

In some embodiments, the system 10 includes a user device 60. The user device 60 may be a smartphone, a tablet, a wearable device such as a smart watch, a desktop computer, a laptop computer, or another type of user device. The user device 60 may be configured to communicate with the transceiver 30 directly or to communicate over the network 232. In some embodiments, the user interface 220 of the transceiver 30 includes some or all of the functionality of the user device 60. In some embodiments, the user device 60 may be used to view information (e.g., the health measurement data, the data and time data, etc.) stored in the database 40. The user device 60 may access the database 40 directly (e.g., if the database 40 is located on the user device 60), or the user device 60 may access the database 40 indirectly through the network 232. In some embodiments, using a display, the user device 60 is configured to provide a graphical user interface to the user (e.g., through an application, through a web page viewed in an internet browser, etc.) for viewing the health measurement data. In other embodiments, the controller 70 is configured to command the user device 60 to provide a notification to the user (e.g., an email, a text message, a notification provided by an application, a sound, a phone call, etc.) in order to notify the user of the occurrence of an event. The system 10 may include multiple user devices 60, each configured to access the database 40 and/or receive notifications.

In the embodiment shown in FIG. 1, the controller 70 is included in the remote storage 50. However, in other embodiments, the controller 70 is included in one or more of the transceiver 30, the remote storage 50, and the user device 60. Alternatively, the controller 70 may be implemented as a standalone device. In some embodiments, the controller 70 is configured to perform an analysis of the health measurement data. In some embodiments, the controller 70 is configured to retrieve health measurement data from the database 40 and analyze the progression of the data over time. The controller 70 may calculate and/or provide the user with averages, trends, statistics, or other information relating to the health measurement data. The health measurement data and the results of the analysis may be shown graphically through a GUI of the user device 60 or the transceiver 30. Accordingly, the controller 70 may be configured to issue commands to other components. By way of example, the controller 70 may issue commands to the transceiver 30, the remote storage 50, and the user device 60.

The processor 72 and the memory device 74 are configured to cooperate to perform the functions of the controller 70. The processor 72 can be implemented as a general purpose processor, an application specific integrated circuit (ASIC), one or more field programmable gate arrays (FPGAs), a group of processing components, or other suitable electronic processing components. The processor 72 may issue commands to other components, analyze data (e.g., the health measurement data), and control the distribution of data throughout the system 10 (e.g., receive health measurement data from the transceiver 30 and transfer the data to the database 40). The memory device 74 (e.g., memory, memory unit, storage device, etc.) is one or more devices (e.g., RAM, ROM, flash memory, hard disk storage, etc.) for storing data and/or computer code for completing or facilitating the various processes, layers and modules described in the present application. The memory device 74 may be or include volatile memory or non-volatile memory. The memory device 74 may include database components, object code components, script components, or any other type of information structure for supporting the various activities and information structures described in the present application. The memory device 74 may be dedicated to the processor 72, or may be a portion of a memory device of another component (e.g., a memory device may be shared between the transceiver 30 and the controller 70).

The controller 70 may compare recently measured health measurement data relating to an individual to healthy ranges of health measurement data. In some embodiments, the controller 70 determines the healthy ranges for the individual using previous health measurement data corresponding to the individual (e.g., a portion of the health measurement data taken when the individual was known to be healthy, an average or trend in the health measurement data, etc.). In some such embodiments, the controller 70 is configured to determine that the current health measurement data is outside of the healthy range if the current health measurement data strays too far from predicted or average values or otherwise indicates that the individual is suffering from an illness. By way of example, if the body temperature of an individual exceeds a certain threshold temperature relative to the average measured body temperature of the individual (e.g., calculated using all of the previous health measurement data, calculated using the health measurement data gathered over a specified period, etc.), the controller 70 may determine that the body temperature is outside of a healthy range. By way of another example, if an individual is stationary or near stationary for a threshold period of time, the controller 70 may determine that the movement level of the individual is outside of a healthy range.

Additionally or alternatively, the controller 70 determines the healthy ranges using standard values of healthy ranges for the similar individuals. Similar individuals may be individuals of the same species, age, sex, occupation, or activity level, individuals with similar medical conditions or histories, or may otherwise be similar to the individual associated with the implant 20. The standard values of healthy ranges may be published values (e.g., from medical journals or other sources). The standard values may be stored locally in a component of the system 10 (e.g., the transceiver 30, the database 40, the remote storage 50, the user device 60, etc.) or may be accessed through the internet or another network connected to the network 232.

The controller 70 may vary the healthy ranges based on a number of factors. The factors may include outside factors such as the associated date or the associated time when the health measurement data was measured (e.g., determined using date and time data from the clock 182) or the outside temperature (e.g., as retrieved from the internet). By way of example, the controller 70 may vary healthy ranges for the body temperature, the blood pressure, the heart rate, and the movement level of the individual to be lower during sleeping hours. By way of another example, when the system 10 is used to monitor the health of a hibernating animal, such as a bear, the controller 70 may vary the healthy range of movement level for to be lower (i.e., less active) during winter months. The healthy ranges for the health measurement data measured at a first point in time may be based on portions of the health measurement data (e.g., the body temperature, the blood glucose level, the heart rate, the movement level, the blood pressure, etc.) measured at the first point in time or at a second point in time near the first point in time. By way of example, the controller 70 may vary the healthy ranges based on current or recent movement level of the individual. The controller 70 may raise the healthy ranges for the heart rate, the body temperature, or the blood pressure of the individual upon determining that the individual has an active movement level (e.g., associated with running).

The controller 70 may be configured to send a command to a component of the system 10 (e.g., the transceiver 30, the remote storage 50, the user device 60, etc.) commanding the component to provide a notification (e.g., a graphic, a sound, a vibration, etc.) to the user if any of the current health measurement data falls outside of the healthy ranges. By way of a first example, the user device 60 may be a smartphone, and the notification may be a push notification provided through a graphical user interface of the smartphone. By way of another example, the notification may be a graphic displayed in a graphical user interface of a display of the transceiver 30. By way of another example, the user device 60 may be a telephone, and the notification may be a call placed to a user device 60. By way of yet another example, the user devices 60 may include multiple cellular phones, and the notification may be a text message sent to the multiple cellular phones.

Figure 4:
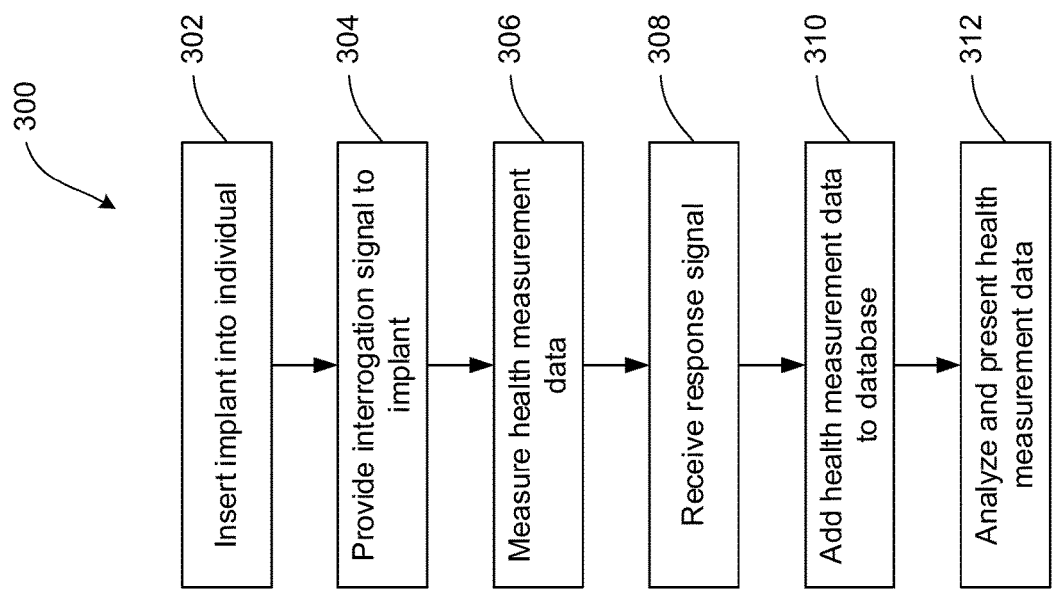
FIG. 4 is a block diagram illustrating a method of using the health information measurement system of FIG. 1.

Referring to FIG. 4, a method 300 of using the system 10 is illustrated. In step 302, the implant 20 is inserted into the individual. In one embodiment, the implant 20 is inserted subcutaneously into the individual using a hypodermic needle and a syringe. The implant 20 is loaded into the hypodermic needle, and the needle is used to puncture the skin. The syringe is then depressed, forcing the implant 20 under the skin and into the body of the individual.

In step 304, the transceiver 30 provides an interrogation signal to the implant 20. The individual and/or the transceiver 30 are moved such that the implant 20 comes within a threshold distance of the transceiver 30. The exact value of the threshold distance between the implant 20 and the transceiver 30 during the step 304 may vary depending upon the application. In some embodiments, the transceiver 30 contacts the surface of the body directly adjacent the implant 20. In other embodiments, the transceiver 30 is separated a greater distance (e.g., 1 inch, 1 foot, 5 feet, etc.) from the implant 20. The transceiver 30 emits the interrogation signal, and the implant 20 receives the interrogation signal. In some embodiments, the transceiver 30 constantly emits the interrogation signal. In other embodiments, the transceiver 30 emits the interrogation signal upon receiving a command from a user through the user interface 220. The interrogation signal may be supplied to the implant 20 for a period of time long enough for the implant 20 to complete a series of measurements, or the interrogation signal may be supplied to the implant 20 for an extended period of time to facilitate charging the energy storage device 180.

In step 306, the implant 20 is configured to measure one or more types of health measurement data and/or date and time data. The types of health measurement data (e.g., body temperature, movement level, etc.) may vary depending on the types of sensors included in the sensor module 150. The controller 170 is configured to control the sensors in the sensor module 150 to perform the measurements and store the health measurement data and/or the corresponding date and time data in the memory device 174. In some embodiments, the controller 170 is configured to begin the measurement upon receiving the interrogation signal. In other embodiments, the controller 170 is configured to perform a measurement on a time basis. The controller 170 may perform a measurement a certain period of time after receiving the interrogation signal, at a certain time of day, or periodically at certain time intervals. The controller 170 may cooperate with the clock 182 to determine when to perform measurements. In some embodiments, multiple sets of health measurement data are stored in the memory device 174 prior to transferring the data to the transceiver 30. Although step 306 is shown after step 304, it should be understood that the implant 20 may measure health measurement data any time after the implant 20 is inserted into an individual.

In step 308, the implant 20 emits a response signal to the transceiver 30 containing the health measurement data and/or the date and time data. The controller 170 cooperates with the interface portion 176 to send the response signal. In some embodiments, the implant 20 continuously emits a response signal. In other embodiments, the implant 20 begins emitting the response signal in response to receiving an interrogation signal, facilitating an energy savings. The transceiver 30 may indicate to the implant 20 through the interrogation signal that the health measurement data has been received successfully. Upon receiving this indication, the controller 170 may erase the health measurement data from the memory device 174 to free up capacity of the memory device 174.

In step 310, the health measurement data and/or the date and time data is added to the database 40. In embodiments where the database 40 is stored on the transceiver 30, the controller 70 may be located in the transceiver 30 and cooperate with the database 40 to store the health measurement data in the database 40 directly. In embodiments where the database 40 is located on another device (e.g., in the remote storage 50, on the user device 60, on another transceiver 30, etc.), the transceiver 30 is configured to communicate with the other device using the network interface 230. The network interface 230 may transfer the health measurement data to the other device directly (e.g., through a USB cable directly linking the two devices, through a Bluetooth connection, etc.) or through the network 232 (e.g., over a local area network, over the internet, etc.). Once the health measurement data and/or the date and time data reaches the other device, the controller 70 in the other device cooperates with the database 40 to store the health measurement data in the database 40. The database 40 stores the data cumulatively (e.g., adds new data to previously stored data each time).

In step 312, the controller 70 analyzes the health measurement data and provides the data to the user. The controller 70 may provide the data directly and/or may provide the results of the analysis. In some embodiments, the controller 70 commands another device (e.g., the user device 60, the transceiver 30, etc.) to display the health measurement data and/or the results of the analysis in a GUI. In some embodiments, the controller 70 determines a healthy range for the health measurement data and notifies the user through the user device 60 or the transceiver 30 if the current health measurement data fall outside of the healthy ranges. The method 300 may be arranged in various loops. By way of example, the method 300 may return to step 304 after completing step 312. By way of another example, the method 300 may return to step 304 after completing step 310.

Referring to FIGS. 5-10, in some embodiments, the system 10 is configured to monitor the health of a pet or domestic companion animal (e.g., a cat, a dog, a rabbit, etc.), shown as dog 400. In some such embodiments, such as the embodiment shown in FIG. 5, the transceiver 30 is incorporated into a handheld scanner 402, and a user manually uses the transceiver 30 to retrieve the health measurement information of the pet from the implant 20. In other such embodiments, the transceiver 30 is incorporated into (e.g., attached to, placed inside of, etc.) an object that the pet interacts with frequently, such as an animal accessory (e.g., a feeding apparatus, shown in FIG. 6 as a food bowl 404, a toy 406, etc.), a piece of furniture (e.g., shown in FIG. 7 as a bed 408, etc.), a semi-permanent structure (e.g., shown in FIG. 8 as a fence 410, etc.), or a portion of a building (e.g., shown in FIG. 9 as a door 412, a door frame 414, and a wall 416, etc.). In such an arrangement, the transceiver 30 may gather the health measurement data and provide power to the implant 20 whenever the pet is within a threshold distance (e.g., 10 feet, 5 feet, 1 foot, etc.) from the transceiver 30 that facilitates communication between the implant 20 and the transceiver 30 (e.g., when the pet is sleeping on the bed 408, eating out of the food bowl 404, or passing through the door frame 414, etc.). In other such embodiments, the transceiver 30 is incorporated into an item configured to be worn by the pet, shown in FIG. 10 as a collar 418. In such an arrangement, the item is configured to hold the transceiver 30 within the threshold range of the implant 20, thereby facilitating constant or near-constant communication with the implant 20 and providing the transceiver 30 with frequent access to health measurement data. In any of these arrangements, the transceiver 30 may then transfer the health measurement data to the database 40 automatically after coming within the threshold distance of the implant 20. Any one of multiple users (e.g., members of a family that own the pet, a veterinarian, etc.) may view the database 40 or receive notifications through a user device 60 such as a phone or tablet.

Figure 11:
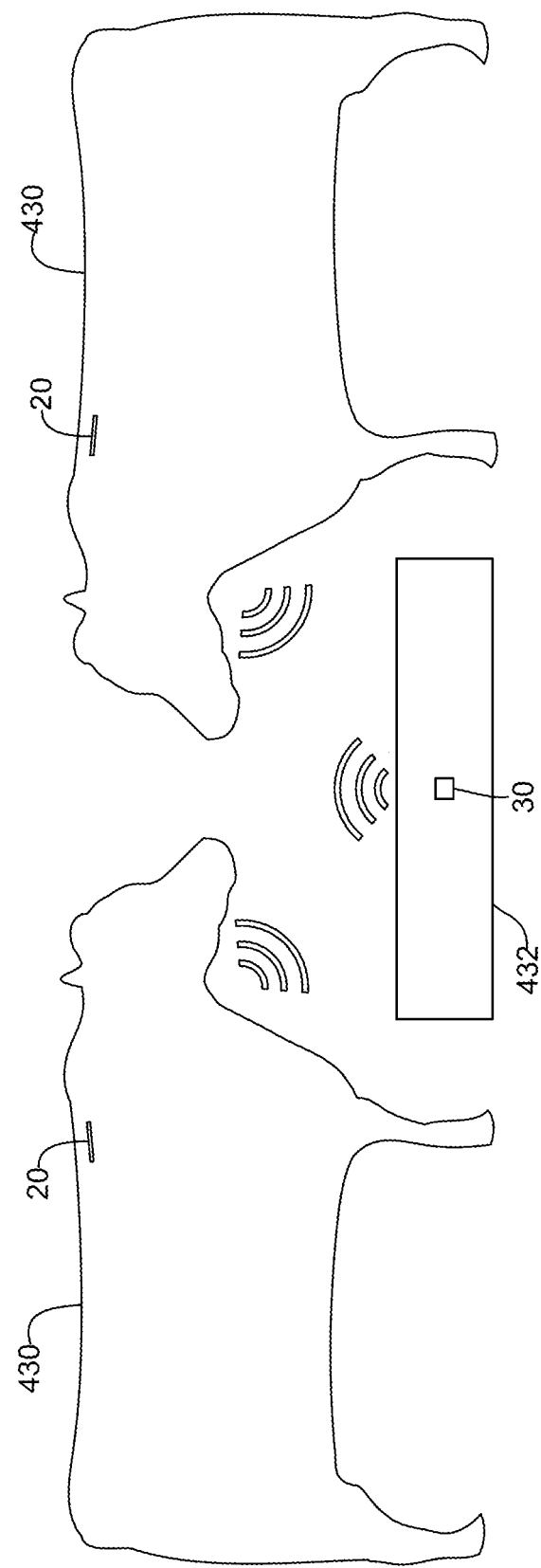
FIG. 11 is a side view showing an arrangement of the implant of FIG. 2A and the transceiver of FIG. 3 configured to monitor a health of a pair of cattle, according to an exemplary embodiment.
Figure 12:
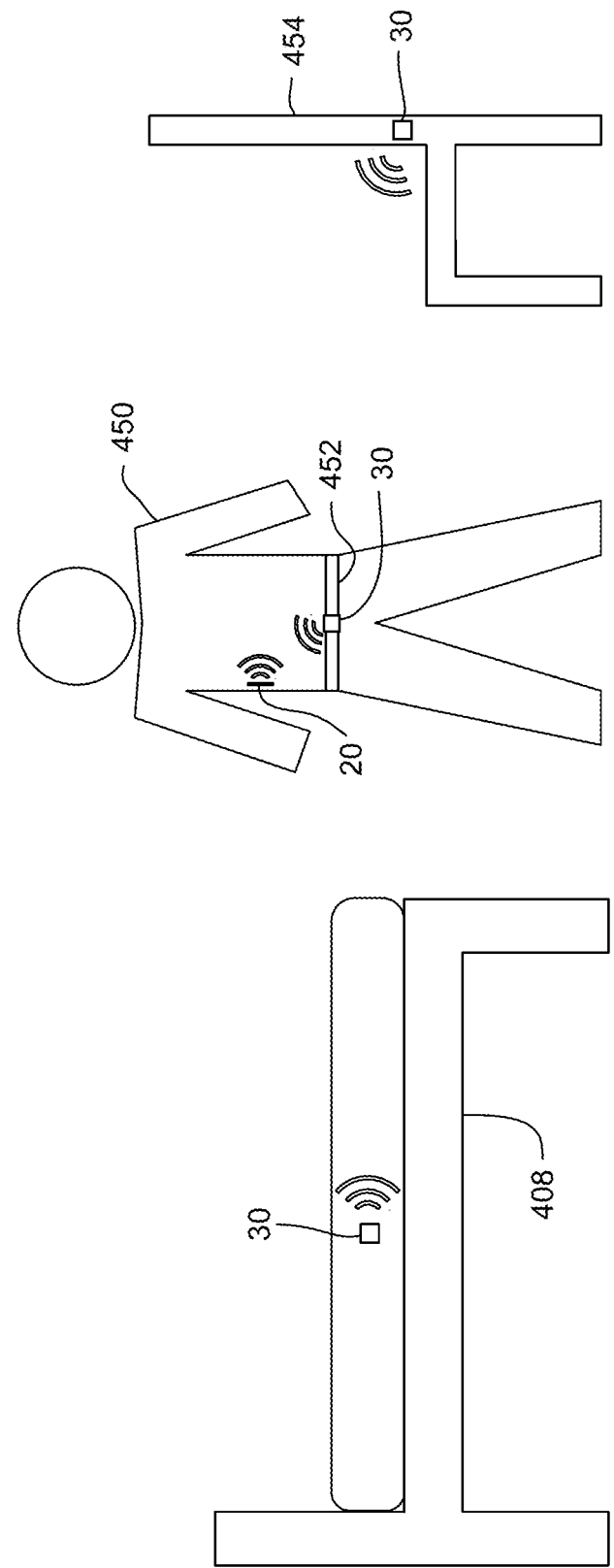
FIG. 12 is a side view showing an arrangement of the implant of FIG. 2A and the transceiver of FIG. 3 configured to monitor a health of a human, according to an exemplary embodiment.

In other embodiments, the system 10 is configured to monitor the health of one or more farm animals or zoo animals (e.g., a herd of cattle, a team of horses, a flock of birds, etc.), shown in FIG. 11 as cattle 430. Each steer or cow 430 is implanted with an implant 20 having a unique identifier. Similar to the embodiments discussed above, the transceiver 30 may be incorporated into a handheld scanner 402, an object that the animals interact with frequently, such as an animal accessory (e.g., a feeding apparatus, shown in FIG. 11 as a feeding trough 432, a toy 406, etc.), a piece of furniture (e.g., a bed 408, etc.), a semi-permanent structure (e.g., a fence 410 or other type of animal containment apparatus, etc.), or a portion of a building (e.g., a door 412, a door frame 414, a wall 416, etc.), or into a wearable device (e.g., a collar 418). The transceivers 30 may transfer the health measurement data to the database 40 automatically. When transferring the health measurement data, the controller 70 may automatically associate the health measurement data with the corresponding unique identifier to categorize the data based on the identity of each individual animal. Any one of multiple users may view the health measurement data or receive notifications concerning the health of the animals through any of multiple user devices 60. By automatically measuring and associating the health measurement data with a particular individual, the system 10 may facilitate monitoring the health of a large number of individuals with only a few users.

In other embodiments, the system 10 is configured to monitor the health of a human (e.g., an astronaut, a human afflicted with an illness that requires frequent monitoring, a fitness enthusiast, etc.), shown in FIG. 12 as human 450. In the system 10, the human 450 may be both the individual and the user. In some embodiments, the system 10 includes a transceiver 30 incorporated into a handheld scanner 402. The human 450 may initiate a transfer of health measurement data from an implant 20 in their body to the transceiver 30 by holding the handheld scanner 402 near their body and interacting with the user interface 220. In other embodiments, the system 10 includes a transceiver 30 that is configured to be worn by the human (e.g., shown in FIG. 12 as a belt 452) or a transceiver 30 that is incorporated into an object that the human 450 interacts with frequently, such as a piece of furniture (e.g., a bed 408, a chair, shown in FIG. 12 as chair 454, etc.), a semi-permanent structure (e.g., a fence 410, etc.), or a portion of a building (e.g., a door 412, a door frame 414, a wall 416, etc.). In some embodiments, the transceiver 30 automatically initiates a connection between the implant 20 and the transceiver 30. Such embodiments facilitate the human 450 or another user, such as a doctor, monitoring the health of the human 450 without having to manually perform measurements, freeing the human 450 to perform other tasks or leisure activities. This is especially useful during time-critical situations (e.g., space travel) as it allows the human 450 to use their time more efficiently instead of taking time to manually evaluate their health on a regular basis.

The present disclosure contemplates methods, systems, and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such connection is properly termed a machine-readable medium. Combinations of the above are also included within the scope of machine-readable media. Machine-executable instructions include, for example, instructions and data which cause a general purpose computer, special purpose computer, or special purpose processing machines to perform a certain function or group of functions.

As utilized herein, the terms "approximately", "about", "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the invention as recited in the appended claims.

It should be noted that the terms "exemplary" and "example" as used herein to describe various embodiments is intended to indicate that such embodiments are possible examples, representations, and/or illustrations of possible embodiments (and such term is not intended to connote that such embodiments are necessarily extraordinary or superlative examples).

The terms "coupled," "connected," and the like, as used herein, mean the joining of two members directly or indirectly to one another. Such joining may be stationary (e.g., permanent, etc.) or moveable (e.g., removable, releasable, etc.). Such joining may be achieved with the two members or the two members and any additional intermediate members being integrally formed as a single unitary body with one another or with the two members or the two members and any additional intermediate members being attached to one another.

References herein to the positions of elements (e.g., "top," "bottom," "above," "below," "between," etc.) are merely used to describe the orientation of various elements in the figures. It should be noted that the orientation of various elements may differ according to other exemplary embodiments, and that such variations are intended to be encompassed by the present disclosure.

Also, the term "or" is used in its inclusive sense (and not in its exclusive sense) so that when used, for example, to connect a list of elements, the term "or" means one, some, or all of the elements in the list. Conjunctive language such as the phrase "at least one of X, Y, and Z," unless specifically stated otherwise, is otherwise understood with the context as used in general to convey that an item, term, etc. may be either X, Y, Z, X and Y, X and Z, Y and Z, or X, Y, and Z (i.e., any combination of X, Y, and Z). Thus, such conjunctive language is not generally intended to imply that certain embodiments require at least one of X, at least one of Y, and at least one of Z to each be present, unless otherwise indicated.

It is important to note that the construction and arrangement of the systems as shown in the exemplary embodiments is illustrative only. Although only a few embodiments of the present disclosure have been described in detail, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements. It should be noted that the elements and/or assemblies of the components described herein may be constructed from any of a wide variety of materials that provide sufficient strength or durability, in any of a wide variety of colors, textures, and combinations. Accordingly, all such modifications are intended to be included within the scope of the present inventions. Other substitutions, modifications, changes, and omissions may be made in the design, operating conditions, and arrangement of the preferred and other exemplary embodiments without departing from scope of the present disclosure or from the spirit of the appended claim.

What is claimed is:
1. A system, comprising:
an implant configured to be inserted subcutaneously into an animal, the implant including:
an antenna;

a sensor module configured to measure data relating to a health of the animal;

an energy storage device configured to store energy and provide the stored energy to the sensor module; and a housing containing the sensor module, the energy storage device, and the antenna, wherein the housing is configured to be positioned subcutaneously in the individual during operation of the sensor module such that the housing is not exposed to an atmosphere surrounding the individual;

at least one of a piece of furniture or a portion of a building comprising a transceiver configured to communicate wirelessly with the implant, the transceiver including a user interface including a touchscreen configured to receive user inputs, wherein the at least one of the piece of furniture or the portion of the building is positioned at a first location, wherein the transceiver is configured to:

provide a first wireless signal to the antenna of the implant in response to the user interface receiving a first user input, the first wireless signal including a first command that causes the antenna of the implant to wirelessly transmit to the transceiver the data relating to the health of the animal and a unique identifier corresponding to the animal;

provide a second wireless signal to the antenna of the implant in response to the user interface receiving a second user input, the second wireless signal including a second command that causes the implant to modify the unique identifier, wherein the first wireless signal and the second wireless signal each convey energy that is at least one of (a) stored in the energy storage device and (b) consumed by the sensor module; and a database provided within a remote storage device positioned at a second location different from the first location, wherein the database is operatively coupled to the transceiver via at least one of the Internet and a cellular network and configured to receive the data relating to the health of the animal from the transceiver and store the data relating to the health of the animal and contact information for an owner of the animal;

wherein the remote storage device comprises a processing circuit configured to:

access the database and provide the data relating to the health of the animal to a user; and identify the contact information for the owner of the animal using the unique identifier.

2. The system of claim 1, wherein the sensor module comprises:

a temperature sensor configured to measure a body temperature of the animal;

a blood glucose sensor configured to measure a blood glucose level of the animal;

a heart rate sensor configured to measure a heart rate of the animal; and a movement sensor configured to measure a movement level of the animal;

wherein the data relates to the body temperature of the animal, the blood glucose level of the animal, the heart rate of the animal, and the movement level of the animal; and wherein the processing circuit is configured to determine whether the body temperature, the blood glucose level, the heart rate, and the movement level of the animal are each within healthy ranges, and wherein the processing circuit is configured to provide a notification to the user in response to a determination that at least one of the body temperature, the blood glucose level, the heart rate, and the movement level of the animal fall outside of the healthy ranges.

3. The system of claim 2, wherein the processing circuit is configured to determine the healthy ranges using at least one of (a) previous data relating to the health of the animal and (b) standard healthy range values for similar animals.

4. The system of claim 3, wherein the implant further includes a timekeeper configured to provide date and time data relating to a passage of time, and wherein the processing circuit is configured to use the date and time data to associate the data relating to the health of the animal with an associated date and an associated time at which the data was measured.

5. The system of claim 4, wherein the processing circuit is configured to vary the healthy ranges based on (a) the associated date, (b) the associated time, and (c) a portion of the data relating to the health of the animal that corresponds to the movement level of the animal.

6. A system, comprising:

an implant configured to be inserted subcutaneously into an animal, the implant including:

an antenna;

a sensor module including:

a temperature sensor configured to measure a body temperature of the animal;

a blood glucose sensor configured to measure a blood glucose level of the animal;

a heart rate sensor configured to measure a heart rate of the animal; and a movement sensor configured to measure a movement level of the animal;

wherein the sensor module is configured to provide sensor data including the body temperature of the animal, the blood glucose level of the animal, the heart rate of the animal, and the movement level of the animal;

a timekeeper configured to provide date and time data including a date and a time when the sensor data is measured by the sensor module;

an energy storage device configured to store energy and provide the stored energy to the sensor module;

a memory configured to store the sensor data and the date and time data; and a housing receiving the sensor module, the timekeeper, the energy storage device, the memory, and the antenna, wherein the housing is configured to be positioned subcutaneously in the animal during operation of the sensor module such that the housing is not exposed to an atmosphere surrounding the animal;

at least one of a piece of furniture or a portion of a building comprising a transceiver configured to communicate wirelessly with the implant while the implant is positioned subcutaneously in the individual, the transceiver including a user interface including a touchscreen configured to receive user inputs, wherein the at least one of the piece of furniture or the portion of the building is positioned at a first location, wherein the transceiver is configured to:

provide a first wireless signal to the antenna of the implant in response to the user interface receiving a first user input, the first wireless signal including a first command that causes the antenna of the implant to wirelessly transmit to the transceiver the sensor data, the date and time data, and a unique identifier corresponding to the animal;

provide a second wireless signal to the antenna of the implant in response to the user interface receiving a second user input, the second wireless signal including a second command that causes the implant to modify the unique identifier, and provide a third wireless signal to the antenna of the implant in response to the user interface receiving a third user input, the third wireless signal including a third command that causes the implant to erase the sensor data and the date and time data from the memory, wherein the first wireless signal, the second wireless signal, and the third wireless signal each convey energy that is stored in the energy storage device; and a database provided within a remote storage device Positioned at a second location different from the first location, wherein the database is operatively coupled to the transceiver via at least one of the Internet and a cellular network and configured to receive the sensor data, the date and time data, and the unique identifier from the transceiver, and wherein the database is configured to store the sensor data, the date and time data, an age of the animal, and a sex of the animal;

wherein the remote storage device comprises a processing circuit configured to:

access the database and provide the sensor data of the animal to a user;

identify the age of the animal and the sex of the animal using the unique identifier;

determine a healthy range for the sensor data based on the time data, the age of the animal, and the sex of the animal;

determine whether the sensor data is within the healthy range; and provide a notification to the user in response to a determination that the sensor data is outside of the healthy range.

\* \* \* \* \*